United States Patent
Zhang et al.

(10) Patent No.: US 12,012,590 B2
(45) Date of Patent: Jun. 18, 2024

(54) BACILLUS VELEZENSIS, CULTURE METHOD THEREFOR AND APPLICATION THEREOF

(71) Applicant: SHANDONG INSTITUTE OF POMOLOGY, Tai'an (CN)

(72) Inventors: Qian Zhang, Tai'an (CN); Li Xin, Tai'an (CN); Yilun Chen, Tai'an (CN); Peng Wu, Tai'an (CN); Liangqing Xi, Tai'an (CN); Yushi Chen, Tai'an (CN); Man Zou, Tai'an (CN); Juanxia Yang, Tai'an (CN)

(73) Assignee: SHANDONG INSTITUTE OF POMOLOGY, Tai'an (CN)

( * ) Notice: Subject to any disclaimer, the term of this patent is extended or adjusted under 35 U.S.C. 154(b) by 0 days.

(21) Appl. No.: 17/906,612

(22) PCT Filed: Jul. 15, 2021

(86) PCT No.: PCT/CN2021/106613
§ 371 (c)(1),
(2) Date: Sep. 16, 2022

(87) PCT Pub. No.: WO2022/042121
PCT Pub. Date: Mar. 3, 2022

(65) Prior Publication Data
US 2023/0174925 A1    Jun. 8, 2023

(30) Foreign Application Priority Data
Aug. 28, 2020   (CN) .......................... 202010882213.7

(51) Int. Cl.
| | | |
|---|---|---|
| *C12N 1/20* | (2006.01) | |
| *A01N 63/22* | (2020.01) | |
| *A23B 7/155* | (2006.01) | |
| *C12R 1/07* | (2006.01) | |

(52) U.S. Cl.
CPC ............. *C12N 1/205* (2021.05); *A01N 63/22* (2020.01); *A23B 7/155* (2013.01); *C12R 2001/07* (2021.05)

(58) Field of Classification Search
CPC ................................ A01N 63/22; C12N 1/205
See application file for complete search history.

(56) References Cited

U.S. PATENT DOCUMENTS

| | | | |
|---|---|---|---|
| 2016/0183538 A1* | 6/2016 | Taghavi ................. | A01N 63/22 424/93.46 |
| 2019/0230938 A1 | 8/2019 | Dagher et al. | |

FOREIGN PATENT DOCUMENTS

| | | | | |
|---|---|---|---|---|
| CN | 110699275 | * | 1/2020 | ............... C12N 1/20 |
| CN | 110699275 A | | 1/2020 | |
| CN | 111172080 A | * | 5/2020 | ............... C12N 1/20 |

OTHER PUBLICATIONS

USPTO Sequence Search Results for Seq ID No. 1, 4pgs, ran on Aug. 24, 2023 (Year: 2023).*
Chao-Nan He Antifungal Activity of Volatile Organic Compounds Produced by Bacillus methylotrophicus and Bacillus thuringiensis against Five Common Spoilage Fungi on Loquats Molecules, vol. 25, Issue 15 p. 1-14 Jul. 24, 2020.

* cited by examiner

*Primary Examiner* — Thane Underdahl
(74) *Attorney, Agent, or Firm* — CBM PATENT CONSULTING, LLC

(57) ABSTRACT

It relates to *Bacillus velezensis*, a culture method and use thereof; *Bacillus velezensis* TA-3-BV serving as an endogenous antagonistic strain of sweet cherry for the first time, and a nucleotide sequence of 16S rDNA of the *Bacillus velezensis* TA-3-BV is shown as SEQ ID NO. 1. The *Bacillus velezensis* TA-3-BV has board-spectrum antibacterial activity for sweet cherry, has an inhibitory effect on a variety of pathogenic fungi, and especially has an excellent inhibitory effect on *Rhizopus stolonifer* serving as a soft rot pathogen of sweet cherry, with an inhibition rate of 69.82±1.43%; in addition, the *Bacillus velezensis* TA-3-BV has a good inhibitory effect on the postharvest rot of sweet cherry fruits, can slow down the rot process of fruits, can delay the rot of fruits by 2-3 d, thereby providing a novel method for postharvest preservation of sweet cherry.

4 Claims, 13 Drawing Sheets

Specification includes a Sequence Listing.

BACILLUS VELEZENSIS, CULTURE METHOD THEREFOR AND APPLICATION THEREOF

FIELD OF THE INVENTION

The present disclosure relates to *Bacillus velezensis*, a culture method and use thereof, and belongs to the technical field of microorganisms.

BACKGROUND OF THE INVENTION

Sweet cherry, also known as large cherry and cherry, is a plant in the *Cerasus* subgenus of the *Prunus* genus of the Rosaceae family. Sweet cherry is rich in nutrients, and its soluble protein content is about 589 mg/100 g. Moreover, sweet cherry contains a large amount of Vc and a variety of trace elements, especially contains rich iron elements at about 8 mg/100 g, and have anti-cancer, anti-tumor, and hemoglobin regeneration promoting effects. Sweet cherry pulp is rich in a variety of phenolic compounds including hydroxycinnamic acids, proanthocyanidins, flavonoids, and anthocyanins, has strong antioxidant capacity, and plays a very important role in disease prevention and human health promotion.

Rot caused by pathogenic fungi is a major problem facing the production of the cherry industry, causing rot loss of up to 50% or more of the total loss. At present, the main postharvest diseases of sweet cherry in China include penicilliosis, gray mold, root rot, brown rot, soft rot, black spot, etc., and pathogenic fungi causing the diseases include *Penicillium expansum*, *Monilinia fructicola*, *Botrytis cinerea*, *Rhizopus* sp., *Mucor* sp., *Alternaria alternata*, *Colletotrichum* sp., *Aspergillus niger*, etc. In Tai'an City of Shandong Province, sweet cherries are widely planted, the yield is large, and the economic value is high. However, soft rot of sweet cherry occurs fast and is highly infective, causing serious economic loss and leading to the development delay of the sweet cherry industry. Therefore, it is of great significance to study separation and identification of dominant antagonists for soft rot of sweet cherry, clarify prevention and control methods of soft rot of sweet cherry, and effectively plan prevention and control work. Soft rot of fruits and vegetables reported in China are caused by the infection of *Rhizopus* sp.

Methods for postharvest preservation of sweet cherry mainly include physical preservation methods and chemical preservation methods. The physical preservation methods (low temperature, CA, irradiation, and thermal treatment) have the defects of high cost, short length for preservation, etc. Chemical preservation agents ($CaCl_2$, $ClO_2$, 1-MCP, and plant essential oils) are commonly used for preservation and can achieve an ideal effect, but they will make pathogens develop drug resistance after long term use and have certain food safety hazards. Therefore, it is urgent to develop a low-cost, safe and healthy, and environmentally-friendly method, and microorganism antagonism preservation as a novel preservation method has become current hot research. Among antagonistic microorganisms for the postharvest preservation of sweet cherry, exogenous antagonistic strains, such as *Cryptococcus laurentii* and *Bacillus* spp., are reported in China, while there is no report on endogenous antagonistic strains of sweet cherry.

SUMMARY OF THE INVENTION

In view of the defects in the prior art, the present disclosure provides *Bacillus velezensis*, a culture method and use thereof. *Bacillus velezensis* TA-3-BV of the present disclosure is separated and selected from a healthy "Tieton" sweet cherry, has a good inhibitory effect on *Rhizopus stolonifer* serving as a soft rot pathogen of sweet cherry, with an inhibition rate of 69.82±1.43%, has broad-spectrum antibacterial activity for sweet cherry, and has an inhibitory effect on a variety of pathogenic fungi.

The technical solutions of the present disclosure are as follows.

*Bacillus velezensis* TA-3-BV has been preserved in China General Microbiological Culture Collection Center (CGMCC) on Jul. 17, 2020, with the preservation address of No. 3, Yard 1, West Beichen Road, Chaoyang District, Beijing, and the preservation number of CGMCC NO. 20398 (hereinafter referred to as *Bacillus velezensis* TA-3-BV or Q-84).

According to the present disclosure, preferably, a nucleotide sequence of 16S rDNA of the *Bacillus velezensis* Q-84 is shown as SEQ ID NO. 1.

According to the present disclosure, preferably, a colony of the *Bacillus velezensis* Q-84 is pale yellow, irregular in shape, and opaque.

A culture method of the above *Bacillus velezensis* Q-84 includes the following steps:

picking well-activated *Bacillus velezensis* Q-84 serving as an antagonist, culturing in an LB medium to obtain a seed solution, and inoculating the seed solution into an LB medium for fermentation culture.

According to the present disclosure, preferably, the seed solution is fermented at 35-40° C. and at 150-200 r/min, and further preferably at 37° C. and at 180 r/min.

The above *Bacillus velezensis* Q-84 is used in the prevention and control of a microorganism disease of sweet cherry.

According to the present disclosure, preferably, the microorganism disease of sweet cherry is a fungal disease; and further preferably, the fungal disease is caused by *Rhizopus stolonifer*.

The above *Bacillus velezensis* Q-84 is used in the postharvest preservation of sweet cherry.

The operation and medium that are not described in detail in the present disclosure are all carried out according to the conventional operation and medium in the art.

Beneficial Effects

1. The present disclosure discovers *Bacillus velezensis* Q-84 serving as an endogenous antagonistic strain of sweet cherry for the first time, and the *Bacillus velezensis* Q-84 has board-spectrum antibacterial activity for sweet cherry, has an inhibitory effect on a variety of pathogenic fungi, and especially has an excellent inhibitory effect on *Rhizopus stolonifer* serving as a soft rot pathogen of sweet cherry, with an inhibition rate of 69.82±1.43%.
2. The present disclosure also optimizes a fermentation medium for the *Bacillus velezensis* Q-84, and if the fermentation medium contains the following ingredients: soluble starch at 20.93 g/L, peptone at 16.22 g/L, and sodium chloride at 5.1 g/L, the cell concentration after fermentation is increased by 22% compared with that before optimization.
3. The *Bacillus velezensis* Q-84 of the present disclosure has a good inhibitory effect on the postharvest rot of sweet cherry caused by a microorganism, can slow down the rot process of fruits, can delay the rot of fruits by 2-3 d at room temperature, can also induce disease resistance and oxidation resistance of plants, improve the anti-disease enzyme (PAL, CHI, and GLU) activity to improve disease resistance of plants, improve the antioxidant enzyme (POD) activity and reduce the PPO and LOX activity at the same time to improve oxidation resistance of plants, slow down the postharvest decay of fruits, and improve stress resistance of fruits, thereby providing a low-cost, safe and healthy, and environmentally-friendly novel method for postharvest preservation of sweet cherry.

DETAILED DESCRIPTION OF THE EMBODIMENTS

The technical solutions of the present disclosure will be further described below with reference to the embodiments and the drawings, but the scope of protection of the present disclosure is not limited thereto. Unless otherwise specified, reagents and pharmaceuticals involved in the embodiments are all common products, and experimental operation involved in the embodiments is conventional operation in the art.

Microorganisms involved in the embodiments:

*Bacillus velezensis* TA-3-BV has been preserved in China General Microbiological Culture Collection Center (CGMCC) on Jul. 17, 2020, with the preservation address of No. 3, Yard 1, West Beichen Road, Chaoyang District, Beijing, and the preservation number of CGMCC NO. 20398 (hereinafter referred to as *Bacillus velezensis* TA-3-BV or Q-84).

*Rhizopus stolonifer* serving as a pathogen is a common market product, or is separated and selected from a sweet cherry, and in the present disclosure, *Rhizopus stolonifer* is obtained by the latter.

Media Involved in the Embodiments:

A PDA medium contains 200 g of peeled potato, 20 g of glucose, and 20 g of agar, water is added to make up to 1,000 mL, and the mixture is sterilized at 115° C. for 30 min. A PDB medium contains the same ingredients without agar.

An LB medium contains 10 g of peptone, 5 g of yeast extract, 10 g of sodium chloride, and 20 g of agar, and is boiled in 1,000 mL of deionized water, pH is regulated to 7.0, and the medium is sterilized at 121° C. for 20 min.

An NA medium contains 3 g of beef extract, 10 g of peptone, 5 g of sodium chloride, and 20 g of agar, and is boiled in 1,000 mL of deionized water, pH is regulated to 7.2, and the medium is sterilized at 121° C. for 20 min.

Sweet cherries involved in the embodiments are "Tieton" sweet cherries collected from the Tianping Lake Base (Tai'an) of the Shandong Institute of Pomology; and peaches are collected from Xili Town, Yiyuan County, Zibo City, Shandong Province.

Example 1 Separation and Identification of a Pathogen and its Pathogenicity

1. Separation and Identification of a Pathogen

The surface of a rotten sweet cherry sample was sterilized with 75% medical alcohol, and washed 3 times with sterile water, the sweet cherry was dried by the air, and a small rotten fruit tissue was cut by using a sterile blade and a tweezer, and placed in the center of a resistant (streptomycin or penicillin) PDA medium and cultured thermostatically at 28° C. for 3-4 d. After a colony grew out on the plate, a bacterial block at the edge was picked and placed in another PDA medium, cultured thermostatically at 28° C., and purified several times until a single colony was obtained. The single colony was inoculated onto a slant of a test tube, and stored in a refrigerator at 4° C. for later use. The above operation was carried out in a sterile environment.

Figure 1:
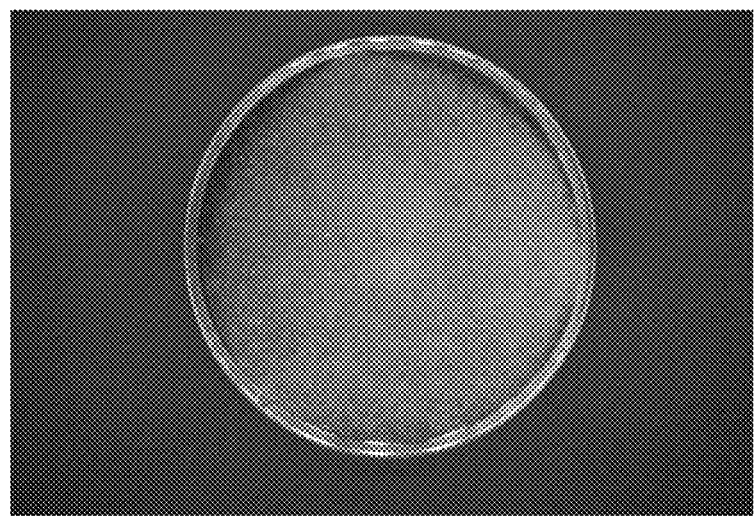
FIG. 1 is an image of the morphology of a colony of *Rhizopus stolonifer* serving as a soft rot pathogen.

The separated and purified pathogen was placed into a PDA medium, and cultured thermostatically at 28° C. for 4 d. It can be found through colonial morphology observation that mycelia of the colony on the PDA plate are white, dry in appearance, opaque, and long and fluffy, aerophilic stolons are distributed on a surface layer of the medium, and black spores are generated, as shown in FIG. 1.

1. Test on the Pathogenicity of the Pathogen

The pathogenicity of the pathogen was determined by the Koch's postulates. The separated and purified pathogen was placed into a PDB test tube, and cultured at 28° C. and at 180 r/min for 48 h to obtain a bacterial suspension at a concentration of $1\times10^6$ CFU/mL. A healthy "Tieton" sweet cherry without any injury on the surface was selected, and immersed in 75% medical alcohol for 20 s, washed 3 times with sterile water, and dried in the air, the equatorial part of the fruit was stabbed by using a sterile toothpick so that a wound of 3×3×3 mm was formed, 10 μL of bacterial suspension ($1\times10^6$ CFU/mL) was sucked up and placed at the wound, after the bacterial suspension was naturally absorbed by the fruit, the fruit was placed into a sealing bag, the pathogen was cultured thermostatically at 28° C. for 3 d, the experiment was repeated 3 times, and diseases conditions were observed.

The fruits can be divided into 5 grades according to the degree of rot, and the grading standards are shown in Table 1.

TABLE 1

Grades of diseases of fruits

| Grades of rot of fruits | Grading standards |
|---|---|
| Grade 0 | The fruit is intact without any rot |
| Grade 1 | The fruit shows mild spots on the surface, and the rot area accounts for less than ⅓ of the surface area of the fruit |
| Grade 2 | The fruit shows obvious rot on the surface, and the rot area accounts for ⅓-½ of the surface area of the fruit |
| Grade 3 | The rot area accounts for more than ½ of the surface area of the fruit, but the fruit is still firm to a certain extent |
| Grade 4 | The fruit is completely rotten |

Figure 2:
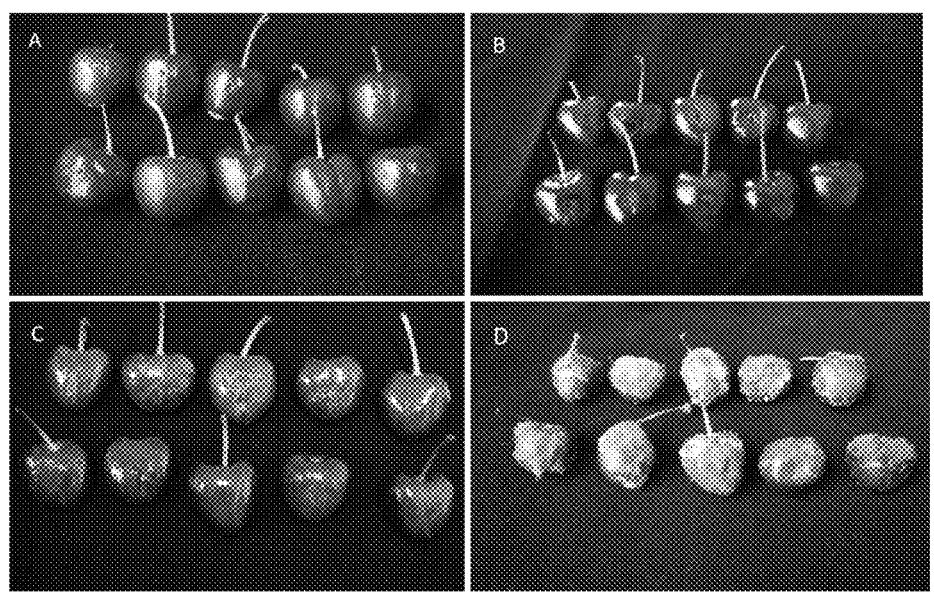
FIG. 2 is an image of disease conditions of cherries after back inoculation of the pathogen, and in the figure, A is an image of the disease conditions of the cherries after 12 h; B is an image of the disease conditions of the cherries after 24 h; C is an image of the disease conditions of the cherries after 36 h; and D is an image of the disease conditions of the cherries after 48 h.

After the back inoculation of the pathogen, the sweet cherries became soft, diameters of the disease spots increased gradually, and white mycelia were generated, and when the sweet cherries were completely rotten, the mycelia turned dark grey. As shown in FIG. 2, the sweet cherries inoculated with the pathogen become soft after 12 h, show obvious disease spots after 24 h, and basically show different degrees of symptoms after 36 h. The disease incidence is 100%, the grade of disease is up to Grade 4, and each fruit is wrapped with dark grey mycelia and completed rotten after 48 h. The disease symptoms after back inoculation are the same as those of soft rot under natural conditions, which indicates that the bacteria are the pathogen causing postharvest soft rot of sweet cherries in Tai'an City, Shandong Province.

1. Biological Identification of the Pathogen

The separated and purified pathogen was inoculated into a PDB medium, and cultured at 28° C. and at 180 r/min for 48 h to obtain a bacterial suspension. 100 mg of mycelium pellets were picked and ground 3 times in liquid nitrogen, DNA was extracted by using a fungal genome kit, and subjected to PCR amplification by using universal primers for fungi, i.e. ITS1 (5'-TCCGTAGGTGAACCTGCGG-3') (SEQ ID NO.: 2) and ITS4 (5'-TCCTCCGCTTATTGA-TATGC-3') (SEQ ID NO.: 3), and a PCR product was purified and sequenced by Rui Biotech Ltd. The sequence was subjected to homology comparison in the GenBank database by using BLAST on NCBI, highly homologous sequences of strains were selected, and a phylogenetic tree was constructed by using MEGA 7.0.

Figure 3:
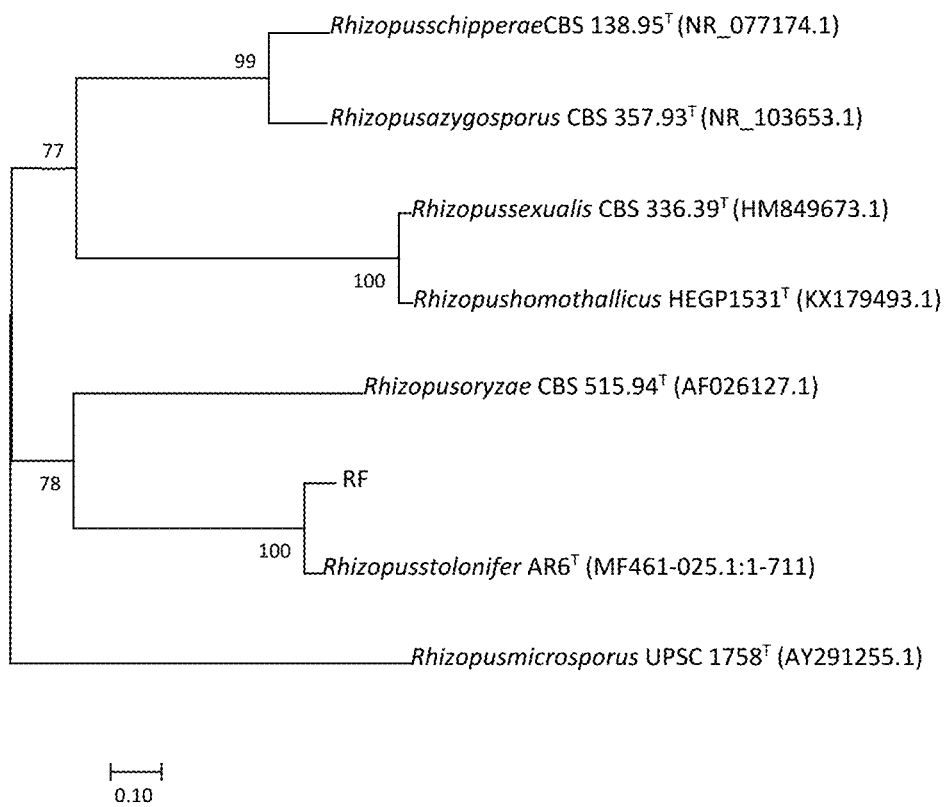
FIG. 3 is a diagram of a phylogenetic tree constructed based on a sequence of the ITS gene of the pathogen, and in the figure, RF refers to the pathogen.

It can be found through the homology comparison of the sequence and construction of the phylogenetic tree that the homology of the sequence of the pathogen and the sequence of *Rhizopus stolonifer* in GenBank is relatively high and reaches 100%. Sequences of ITS of different species of the *Rhizopus* genus in the GenBank database were selected and used as outgroups to construct the phylogenetic tree. It can be found that the pathogenic strain and the closely related *Rhizopus stolonifer* cluster in the same Glade (see FIG. 3). According to the phylogenetic tree in combination with the morphological characteristics of the pathogen during culture, the pathogen is identified as *Rhizopus stolonifer*.

Example 2 Separation, Selection, and Identification of an Antagonist 2.1 Separation and Selection of an Endogenous Antagonist 30 healthy "Tieton" sweet cherries were taken and ground, 1 g of pulp was weighed, and added into 9 mL of sterile normal saline, the mixture was uniformly mixed to obtain a stock solution, and the stock solution was stood for 20 min. The stock solution was diluted by gradient dilution to obtain diluted solutions at concentrations of $10^{-3}$, $10^{-4}$, and $10^{-5}$, respectively, 100 µL of each diluted solution was taken and coated onto an LB medium, 3 parallel samples were set for each gradient, and the diluted solutions were cultured thermostatically at 37° C. for 24 h. After growing out, the colonies were inoculated into another LB medium according to the three-phase streaking pattern, and cultured thermostatically at 37° C. until a single colony was obtained. The single colony was picked onto an LB slant, and after growing out, the colony was stored at 4° C.

A bacterial cake of 6 mm was taken from the PDA plate on which *Rhizopus stolonifer* serving as a pathogen was cultured for 7-10 d by using a filter paper, and inoculated at the center of another PDA plate, a sterile filter paper of 6 mm was placed at a distance of 2.5 cm from the pathogen, 6 µL of fermentation broth of the above separated and purified bacteria was sucked up and dropped onto the filter paper, 3 parallel samples were set on each PDA plate, the PDA plate to which only the pathogen was inoculated was used as a control, the experiment was repeated 3 times, the pathogen was cultured thermostatically at 28° C. for 5-7 d, and diameters of colonies and inhibition rates were observed.

Inhibition rate (%) =

$$\frac{\text{diameter of colony of pathogen of control group} - \text{diameter of colony of pathogen of treatment group}}{\text{diameter of colony of pathogen of control group}} \times 100\%$$

Figure 4:
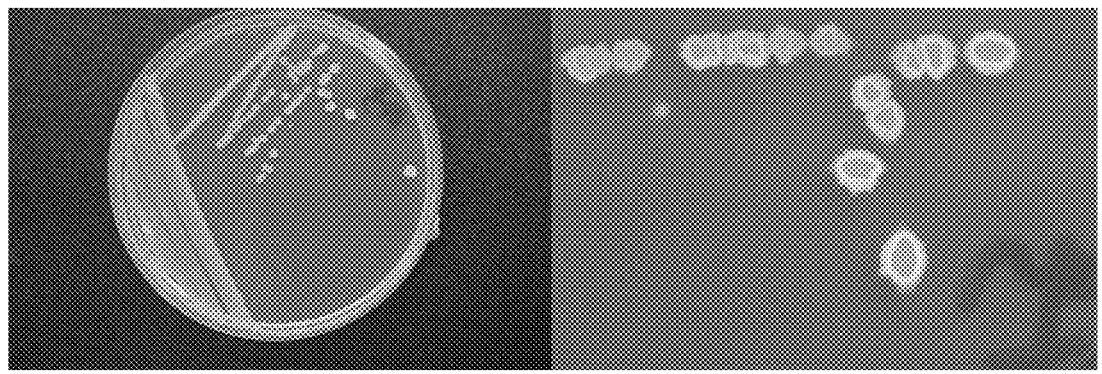
FIG. 4 is an image of the morphology of a colony of *Bacillus velezensis* Q-84.

17 strains of bacteria with different morphology were obtained from the healthy sweet cherry fruits. 3 strains of bacteria that have a certain biocontrol effect on soft rot of sweet cherry were selected from the 17 strains of bacteria. As shown in FIG. 2, the strain Q-84 has the most obvious inhibitory effect on *Rhizopus stolonifer* serving as a soft rot pathogen, with an inhibition rate of 69.82±1.43%, and the diameter of the colony of the pathogen was the smallest and was 1.98±0.17 cm. Under the condition of $P<0.05$, there were significant differences between the treatment group Q-84 and the treatment group Q-2, as well as the treatment group Q-8, and there was no significant difference between the treatment group Q-2 and the treatment group Q-8. It can be found through observation that the biocontrol strain Q-84 is pale yellow, irregular in shape, and opaque (see FIG. 4).

Table 2 Inhibitory effects of the endogenous antagonists on the growth of the soft rot pathogen of sweet cherry

TABLE 2

Inhibitory effects of the endogenous antagonists on the growth of the soft rot pathogen of sweet cherry

| Serial No. | Diameter of colony | Inhibition rate % |
|---|---|---|
| CK | 6.56 ± 0.07[a] | — |
| Q-2 | 5.35 ± 0.23[b] | 18.44 ± 0.77[b] |
| Q-8 | 5.62 ± 0.11[c] | 14.33 ± 0.57[b] |
| Q-84 | 1.98 ± 0.17[b] | 69.82 ± 1.43[a] |

Note:
different lowercase letters in the same column represent significant differences among different treatment groups (p < 0.05).

2.2 Identification of the Endogenous Antagonist

The separated and purified endogenous antagonist Q-84 was placed into an LB medium, and cultured thermostatically at 37° C. for 24 h, and the morphology of a colony was observed. Physiological and biochemical properties of the endogenous antagonist were identified specifically with reference to *Manual of Systematic Identification of Common Bacteria* and *Bergey's Manual of Systematic Bacteriology*. It is found that the physiological and biochemical properties are the same as physiological and biochemical indexes of *Bacillus velezensis*.

DNA of the strain Q-84 was extracted by using a bacterial genome kit, PCR amplification was performed on 16S rDNA of the bacteria by using universal primers for bacteria, i.e. 27F (5'-AGAGTTTGATCCTGGCTCAG-3') (SEQ ID NO.: 4) and 1492r (5'-GGTTACCTTGTTACGACTT-3') (SEQ ID NO.: 5), and a PCR product was detected by 1% agarose gel electrophoresis and sequenced. A nucleotide sequence of 16S rDNA of Q-84 is shown as SEQ ID NO. 1. The sequence was subjected to homology comparison by BLAST in GenBank, and sequences of representative strains were selected, and subjected to cluster analysis by MEGA 7.0 to construct a phylogenetic tree.

Figure 5:
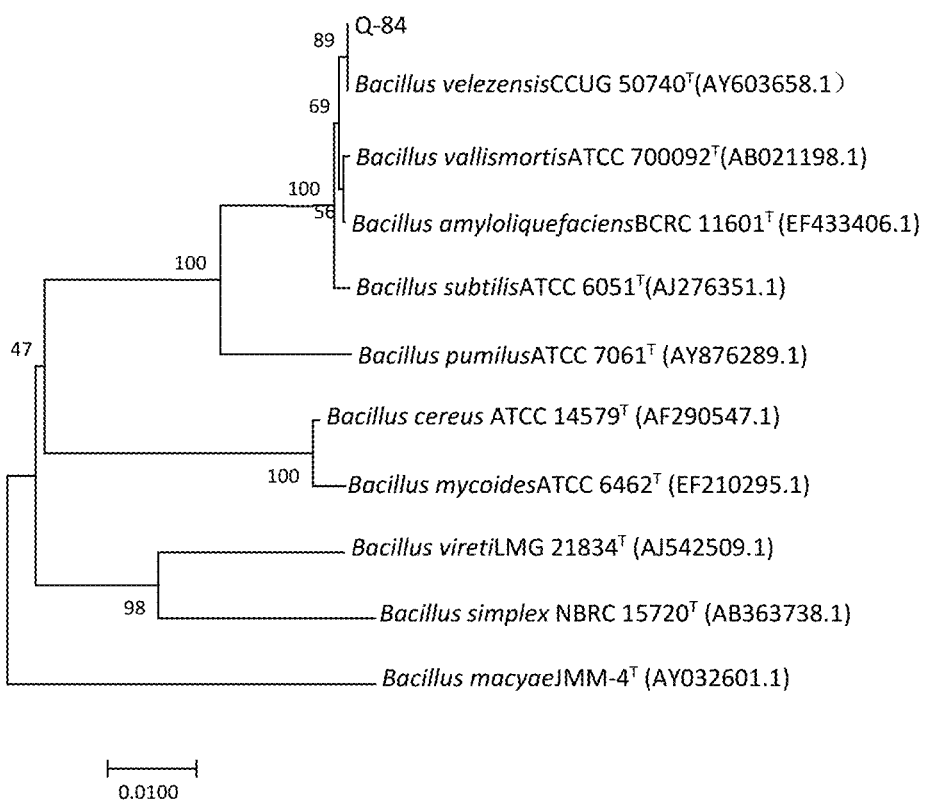
FIG. 5 is a diagram of a phylogenetic tree constructed based on a sequence of the 16S rDNA gene of the *Bacillus velezensis* Q-84.

Results show that the strain Q-84 and *Bacillus velezensis* cluster (see FIG. 5), and the homology is 89%. According to the results in combination with the morphological identification and physiological and biochemical identification results, the strain Q-84 is finally identified as *Bacillus velezensis*.

The above *Bacillus velezensis* Q-84 has been preserved in China General Microbiological Culture Collection Center (CGMCC) on Jul. 17, 2020, with the preservation address of No. 3, Yard 1, West Beichen Road, Chaoyang District, Beijing, and the preservation number of CGMCC NO. 20398.

Figure 6:
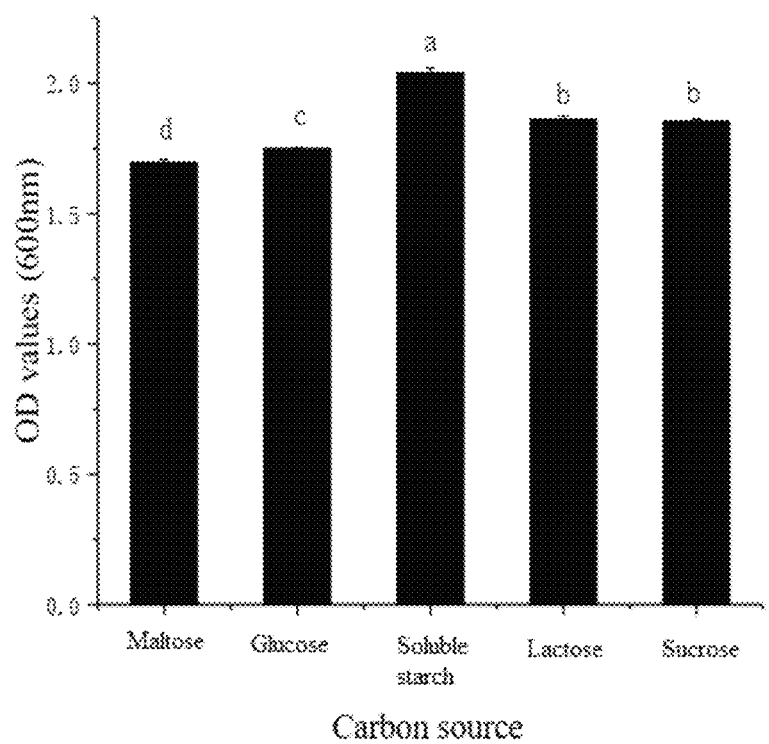
FIG. 6 is a diagram of effects of different carbon sources on the growth of the *Bacillus velezensis* Q-84, and in the figure, different lowercase letters represent significant differences (p<0.05) among different treatment groups.

Example 3 Optimization of Medium for the Antagonist 3.1 Effects of Carbon Sources on the Growth of the Endogenous Antagonist Well-activated *Bacillus velezensis* Q-84 serving as an antagonist were picked, and cultured in an LB medium to obtain a seed solution. NB media were used as basic media, carbon sources in the NB media were replaced with sucrose, glucose, lactose, soluble starch, and maltose at 3 g/L, respectively, other ingredients in the media were kept unchanged, and an NB medium was used as a control. 1 mL of seed solution was sucked up and inoculated into 50 mL of fermentation media containing different carbon sources, placed in a constant temperature shaker at 37° C., and cultured by shaking at 180 r/min for 16 h, and cell concentrations of fermentation broths were determined. Results are shown in FIG. 6, soluble starch serving as the only carbon source is the most beneficial to the growth of *Bacillus velezensis* Q-84, is significantly different from other carbon sources, and followed by lactose, sucrose, glucose, and maltose; there is no significant difference between lactose and sucrose when used as carbon sources; the cell concentration of the fermentation broth is the lowest when maltose is used as a carbon source. Therefore, soluble starch is selected as the most suitable carbon source for a fermentation medium for the *Bacillus velezensis* Q-84.

Figure 7:
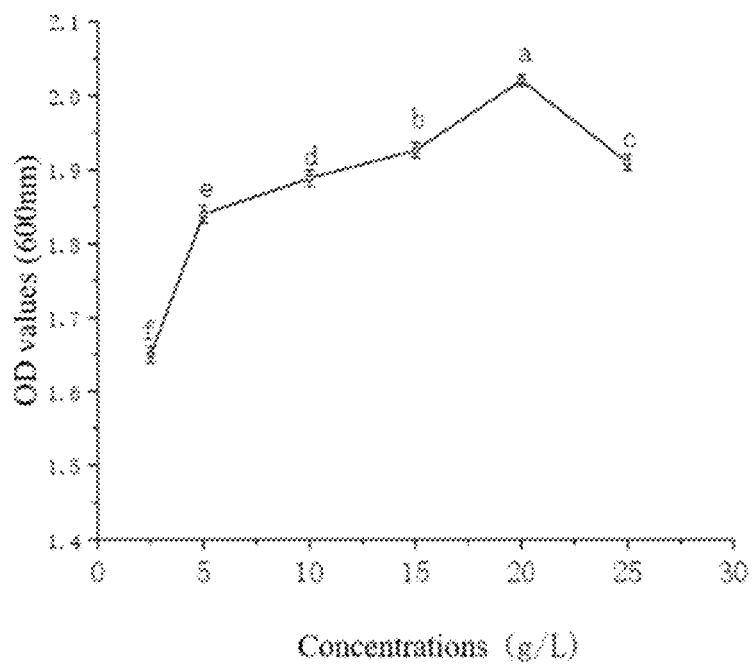
FIG. 7 is a diagram of effects of soluble starch at different concentrations on the growth of the *Bacillus velezensis* Q-84, and in the figure, different lowercase letters represent significant differences (p<0.05) among different treatment groups.

After the optimum carbon source was selected, the addition amount of soluble starch in a fermentation medium was optimized. Concentrations of soluble starch in fermentation media were set as 3 g/L, 5 g/L, 10 g/L, 15 g/L, 20 g/L, and 25 g/L, respectively, the *Bacillus velezensis* Q-84 was cultured and detected by the above method, each treatment was repeated 3 times, and the experiment was repeated twice. Results are shown in FIG. 7, as the concentration of soluble starch is increased, the OD value is increased; when the concentration of soluble starch is increased to 20 g/L, the OD values is the maximum; and when the concentration of soluble starch is higher than 20 g/L, the OD value is decreased. It may be that soluble starch at a high concentration not only promotes the growth of bacteria, but also accumulates a large number of metabolites, which hinders the proliferation of bacteria. Therefore, 20 g/L is selected as the most suitable concentration of soluble starch.

3.2 Effects of Nitrogen Sources on the Growth of the Endogenous Antagonist

Figure 8:
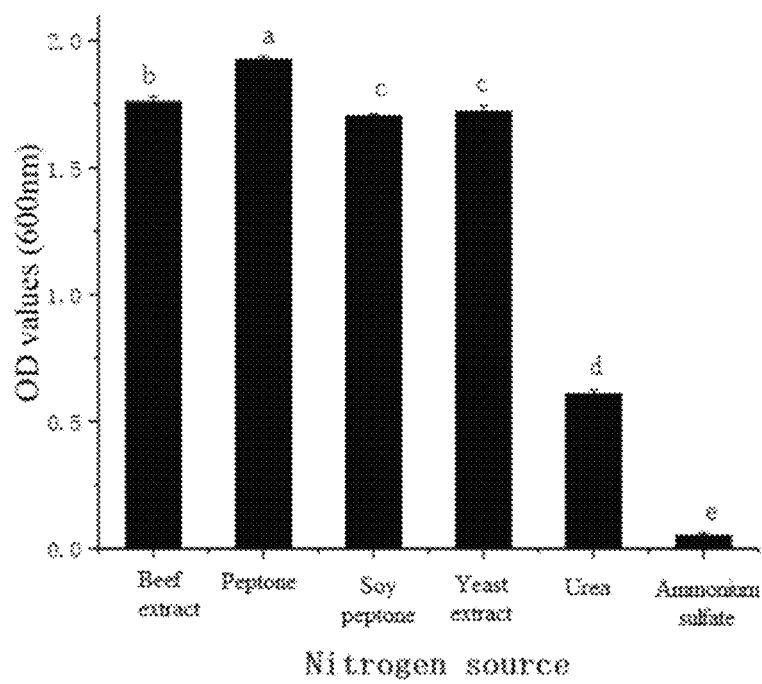
FIG. 8 is a diagram of effects of different nitrogen sources on the growth of the *Bacillus velezensis* Q-84, and in the figure, different lowercase letters represent significant differences (p<0.05) among different treatment groups.

An experimental method was the same as that of 3.1, and a difference was that nitrogen sources in NB media were replaced with beef extract, peptone, soy peptone, yeast extract, urea, and ammonium sulfate at 10 g/L, respectively. Results are shown in FIG. 8, and the OD value is the maximum when peptone is used as the only nitrogen source; and compared with other nitrogen sources, the OD values are obviously lower when urea and ammonium sulfate are used as nitrogen sources, which indicates that the microorganism grows slowly in this environment, and the *Bacillus velezensis* Q-84 has stronger ability to utilize organic nitrogen sources. Based on the above, peptone is selected as the most suitable nitrogen source for a fermentation medium for *Bacillus velezensis*.

Figure 9:
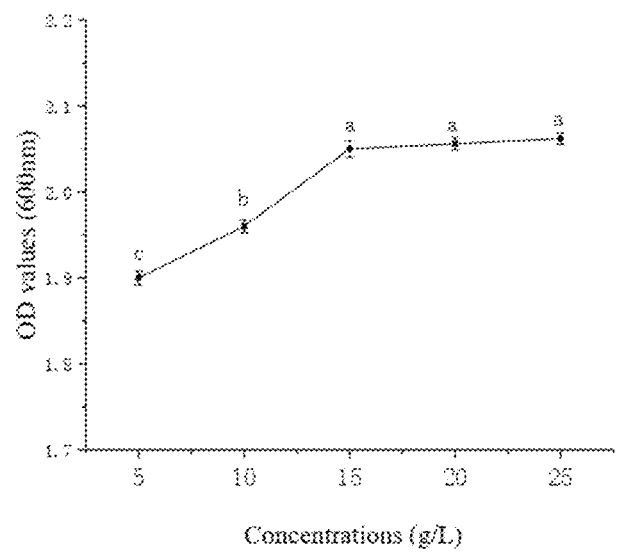
FIG. 9 is a diagram of effects of peptone at different concentrations on the growth of the *Bacillus velezensis* Q-84, and in the figure, different lowercase letters represent significant differences (p<0.05) among different treatment groups.

After the optimum nitrogen source was selected, the addition amount of peptone in a fermentation medium was optimized. Concentrations of peptone in fermentation media were set as 5 g/L, 10 g/L, 15 g/L, 20 g/L, and 25 g/L, respectively, the *Bacillus velezensis* Q-84 was cultured and detected by the above method, each treatment was repeated 3 times, and the experiment was repeated twice. Results are shown in FIG. 9, and as the concentration of peptone is increased, the OD value increases; and when the concentration of peptone is higher than 15 g/L, the OD value changes gently. It indicates that the *Bacillus velezensis* Q-84 can utilize a carbon source at about 15 g/L, an excess nitrogen source does not have much impact on the growth of the microorganism, and 15 g/L is selected as the most suitable concentration of peptone in consideration of cost.

3.3 Effects of Inorganic Salts on the Growth of the Endogenous Antagonist

Figure 10:
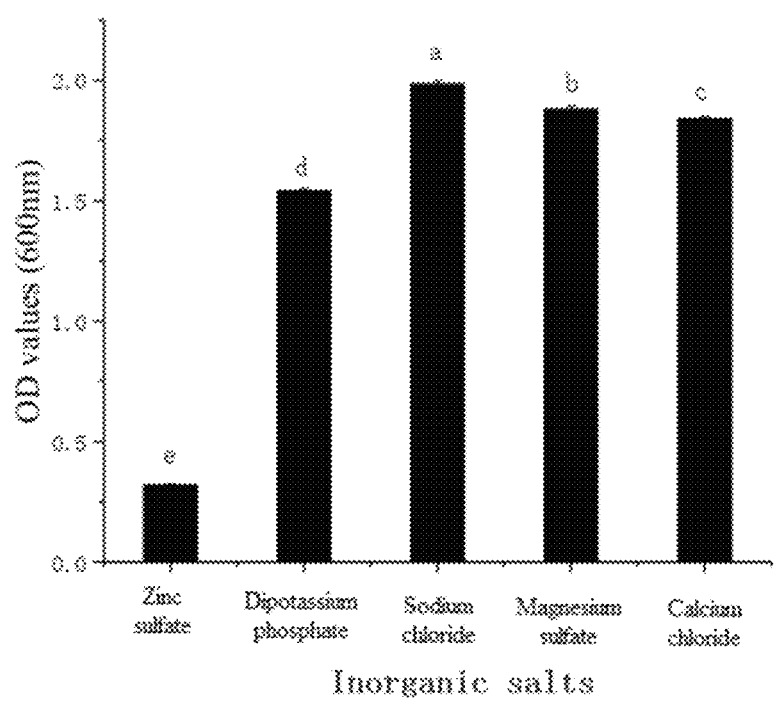
FIG. 10 is a diagram of effects of different inorganic salts on the growth of the *Bacillus velezensis* Q-84, and in the figure, different lowercase letters represent significant differences (p<0.05) among different treatment groups.

An experimental method was the same as that of 3.1, and a difference was that inorganic salts in NB media were replaced with zinc sulfate, dipotassium phosphate, sodium chloride, magnesium sulfate, and calcium chloride at 5 g/L, respectively. Results are shown in FIG. 10, the cell concentration is the highest when sodium chloride is used as the only inorganic salt, followed by magnesium sulfate, calcium chloride, and dipotassium phosphate; and the cell concentration is the lowest when zinc sulfate is used as a trace element for the growth of bacteria. Therefore, sodium chloride is selected as the most suitable inorganic salt for a fermentation medium for the *Bacillus velezensis* Q-84.

Figure 11:
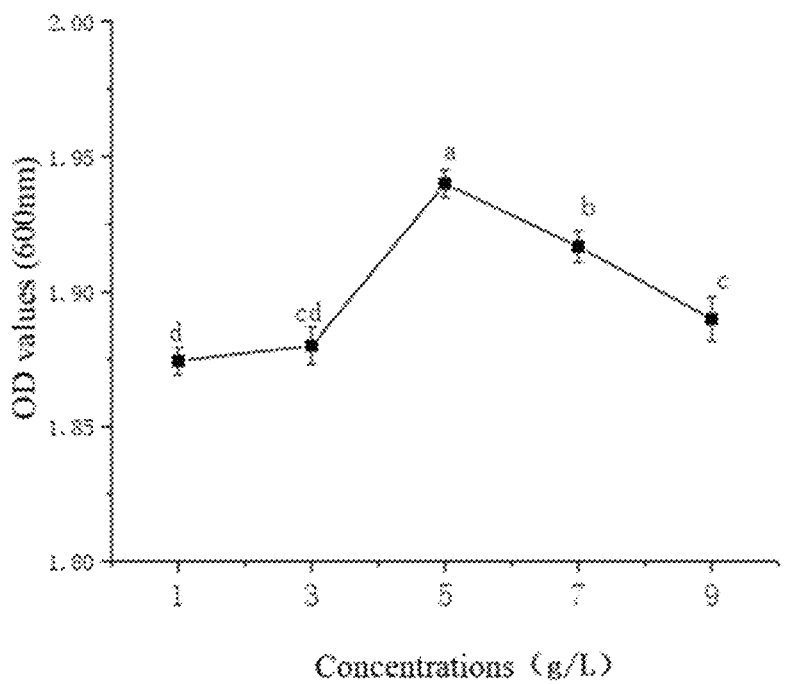
FIG. 11 is a diagram of effects of sodium chloride at different concentrations on the growth of the *Bacillus velezensis* Q-84, and in the figure, different lowercase letters represent significant differences (p<0.05) among different treatment groups.

After the optimum inorganic salt was selected, the addition amount of the inorganic salt in a fermentation medium was optimized. Concentrations of sodium chloride in fermentation media were set as 1 g/L, 3 g/L, 5 g/L, 7 g/L, and 9 g/L, respectively, the *Bacillus velezensis* Q-84 was cultured and detected by the above method, each treatment was repeated 3 times, and the experiment was repeated twice. Results are shown in FIG. 11, and as the addition amount of sodium chloride is increased, the cell concentration shows a trend of first increasing and then decreasing; sodium chloride at a concentration of 5 g/L is the most beneficial to the growth of the bacteria; and the cell concentration is significantly decreased when the concentration of sodium chloride is higher or lower than 5 g/L. Therefore, 5 g/L is selected as the most suitable concentration of sodium chloride.

3.4 Optimization of Growth Conditions for the Endogenous Antagonist by a Response Surface Experiment In order to study effects of soluble starch, peptone, and sodium chloride on the cell concentration of the antagonist, an experiment was carried out according to Table 3. According to experimental results, obtained data were analysed by using Design-Expert 8.0.6.1, and a regression equation was established by taking soluble starch A, peptone B, and sodium chloride C as independent variables and taking $OD_{600}$ value Y as a dependent variable. The equation is as follows:

$$Y = +2.04 + 0.042A + 0.039B + 0.019C + 0.045AB - 0.020AC - 0.018BC - 0.14A^2 - 0.095B^2 - 0.11C^2$$

Variance analysis results are shown in Table 4, a p value of the model is less than 0.0001, the equation model is highly significant, lack of fit P is equal to 0.3387, which is greater than 0.05, and the lack of fit of the model is not significant, which indicates that the established model has high reliability and degree of fitting. Among the primary terms, the soluble starch, the peptone, and the sodium chloride are highly significant; among the interaction terms, a difference between the soluble starch and the peptone is highly significant, a difference between the soluble starch and the sodium chloride is significant, and a difference between the peptone and the sodium chloride is significant; and effects of the quadratic terms soluble starch, peptone, and chloride on the response value $OD_{600}$ are highly significant. A determination coefficient $R^2$ is equal to 0.9938, which indicates that the model can explain 99.38% of experiments, and the regression equation has a high degree of fitting. It can be known from the F value of each factor that the factors affecting the growth of the microorganism satisfy the condition of soluble starch>peptone>sodium chloride.

In order to further verify the reliability of the response surface methodology, 2 fermentation experiments were carried out according to an optimized formula, and an average $OD_{600}$ value of fermentation broths was determined to be 2.04, which was close to the model's predicted value of 2.05, and the cell concentration was increased by 22% compared with that before optimization. The optimized formula of a fermentation medium for the *Bacillus velezensis* Q-84 includes soluble starch at 20.93 g/L, peptone at 16.22 g/L, and sodium chloride at 5.1 g/L.

TABLE 3

BBD experimental design and results

| Experiment No. | A soluble starch/g/L | B peptone/g/L | C sodium chloride/g/L | $OD_{600}$ value |
|---|---|---|---|---|
| 1 | 20.00 | 15.00 | 5.00 | 2.05 |
| 2 | 20.00 | 20.00 | 7.00 | 1.89 |
| 3 | 15.00 | 15.00 | 3.00 | 1.71 |
| 4 | 20.00 | 10.00 | 3.00 | 1.75 |
| 5 | 25.00 | 15.00 | 3.00 | 1.84 |
| 6 | 25.00 | 10.00 | 5.00 | 1.77 |
| 7 | 25.00 | 15.00 | 7.00 | 1.83 |
| 8 | 20.00 | 10.00 | 7.00 | 1.83 |
| 9 | 20.00 | 15.00 | 5.00 | 2.05 |
| 10 | 25.00 | 20.00 | 5.00 | 1.92 |
| 11 | 15.00 | 10.00 | 5.00 | 1.78 |
| 12 | 20.00 | 15.00 | 5.00 | 2.05 |
| 13 | 20.00 | 15.00 | 5.00 | 2.04 |
| 14 | 15.00 | 15.00 | 7.00 | 1.78 |
| 15 | 20.00 | 15.00 | 5.00 | 2.02 |
| 16 | 20.00 | 20.00 | 3.00 | 1.88 |
| 17 | 15.00 | 20.00 | 5.00 | 1.75 |

TABLE 4

Variance analysis of the regression equation

| Sources of variation | Quadratic sum | Degree of freedom | Mean square | F value | P value | Significance |
|---|---|---|---|---|---|---|
| Model | 0.23 | 9 | 0.026 | 124.83 | <0.0001 | Significant |
| A | 0.014 | 1 | 0.014 | 69.52 | <0.0001 | |
| B | 0.012 | 1 | 0.012 | 57.79 | 0.0001 | |
| C | 2.812E−003 | 1 | 2.812E−003 | 13.53 | 0.0079 | |
| AB | 8.100E−003 | 1 | 8.100E−003 | 38.97 | 0.0004 | |
| AC | 1.600E−003 | 1 | 1.600E−003 | 7.70 | 0.0275 | |
| BC | 1.225E−003 | 1 | 1.225E−003 | 5.89 | 0.0456 | |
| $A^2$ | 0.085 | 1 | 0.085 | 409.90 | <0.0001 | |
| $B^2$ | 0.038 | 1 | 0.038 | 181.86 | <0.0001 | |
| $C^2$ | 0.051 | 1 | 0.051 | 243.99 | <0.0001 | |
| Residual | 1.455E−003 | 7 | 2.079E−004 | | | |
| Lack of fit | 7.750E−004 | 3 | 2.583E−004 | 1.52 | 0.3387 | Non-significant |
| Pure error | 6.800E−004 | 4 | 1.700E−004 | | | |
| Total Sum of Squares | 0.23 | 16 | | | | |

Example 4 Antagonistic Effect of the Antagonist on the Pathogen

Activated *Bacillus velezensis* Q-84 was cultured in an LB medium to obtain a seed solution, the seed solution was inoculated into an LB medium at an inoculation rate of 2% and cultured thermostatically by shaking at 37° C. and at 150 r/min for 72 h, the fermentation broth obtained by culture for 72 h was diluted to a concentration of $1\times10^8$ CFU/mL.

Figure 12:
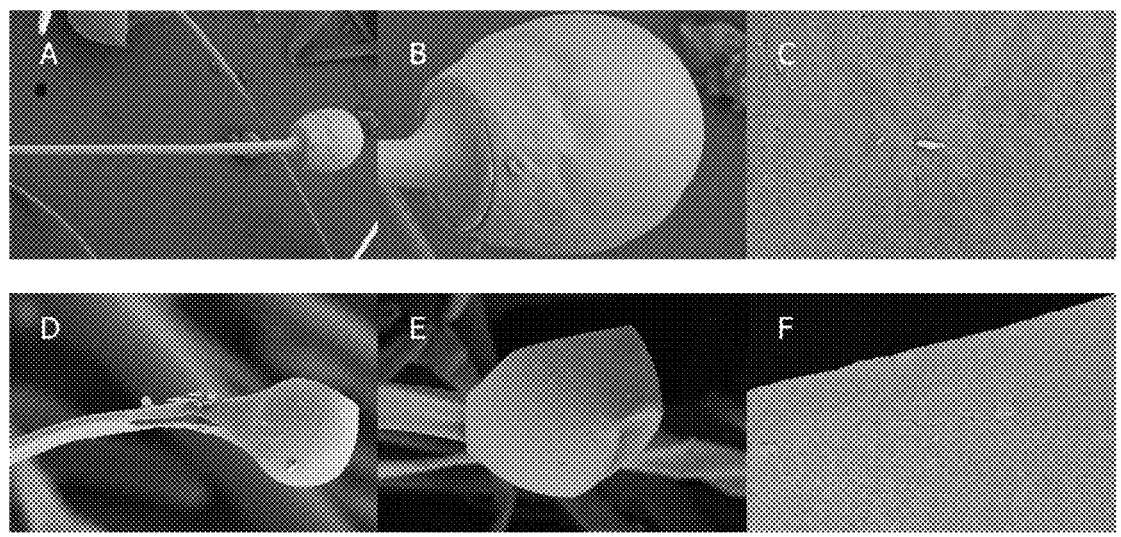
FIG. 12 is an image of an effect of a fermentation broth of the *Bacillus velezensis* Q-84 on the micromorphology of a mycelium of the pathogen, and in the figure, A is an image of a mycelium of a control group (150 magnifications); B is an image of a sporangium of the control group (550 magnifications); C is an image of a sporangium wall of the control group (1000K magnifications); D is an image of a mycelium of a treatment group (150K magnifications); E is an image of a sporangium of the treatment group (120K magnifications); and F is an image of a sporangium wall of the treatment group (1500K magnifications)

A bacterial cake of 6 mm was taken from the PDA plate on which *Rhizopus stolonifer* serving as a pathogen was cultured for 7-10 d by using a filter paper, and inoculated at the center of another PDA plate, a sterile filter paper of 6 mm was placed at a distance of 2.5 cm from the pathogen, 6 μL of diluted fermentation broth of *Bacillus velezensis* Q-84 was sucked up and dropped onto the filter paper, 3 parallel samples were set on each PDA plate, and the pathogen was cultured thermostatically at 28° C. for 60 h. Mycelia around an inhibition zone were picked by using a sterile toothpick and used as a treatment group; and mycelia of the pathogen growing under normal culture conditions were taken as a control group. The mycelia of the antagonist treatment group and control group were taken, fixed with a 2.5% glutaraldehyde solution at 4° C. for 24 h, and placed into ethanol at different concentrations (45%, 55%, 65%, 75%, 85%, 95%, and 100%) in sequences for dehydration for 20 min each time, and the samples were dried by a critical-point drying method, and subjected to metal spraying. The samples were observed under a scanning electron microscope (JCM-7000) and photographed. Results are shown in FIG. 12, and it can be found from the scanning electron microscopy images that there is a big difference in microstructures of the mycelium of the antagonist treatment group and the mycelium of the control group. It can be known from images A and D that the mycelium of the control group (A) is longer, and a sporangiophore is erected and unbranched; and a sporangiophore of the treatment group (D) is broken. It can be known from images B and E that a sporangium of the control group (B) is healthy and plump, nearly spherical, and tuberculate; and a sporangium of the treatment group (E) is deformed with surface depressions, wrinkles, roughness, and unevenness. It can be known from images C and F that the sporangium of the control group (C) has black spots on the rough surface; and the sporangium of the treatment group (F) has cracks on the surface. It indicates that the *Bacillus velezensis* Q-84 serving as an antagonist can destroy the mycelial structure of the pathogen so as to kill the pathogen.

Example 5 Effects of the Endogenous Antagonist on the Natural Postharvest Rot and Storage Quality of Sweet Cherries Postharvest sweet cherry fruits with the same mature degree and uniform size and without mechanical injury were selected, and immersed in a fermentation broth ($10^9$ CFU/mL) of *Bacillus velezensis* Q-84 for 2 min, a control group was treated with sterile water, and natamycin was taken as a positive control. Each treatment group was placed into a transparent preservation box, and stored at 28° C. Disease conditions and quality indexes of the fruits were determined every 3 d. There were 200 fruits in each treatment group, 3 repeats were made for each treatment, and the whole experiment was repeated twice.

Figure 13:
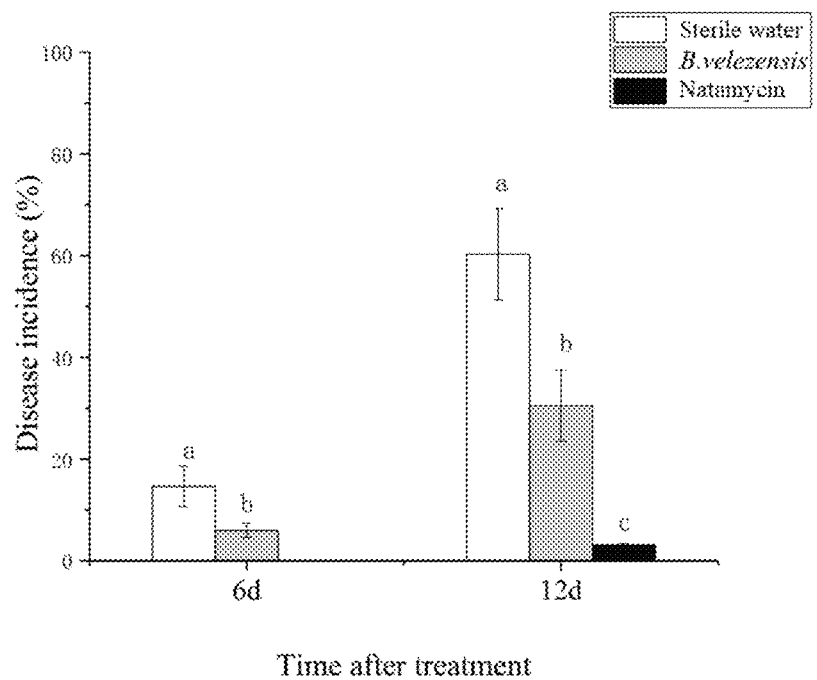
FIG. 13 is a diagram of an effect of *Bacillus velezensis* Q-84 treatment on the natural rot of a sweet cherry fruit, and in the figure, different lowercase letters corresponding to the same time after treatment represent significant differences (p<0.05) among different treatment groups.

Results are shown in FIG. 13, natamycin has the best inhibitory effect on the rot of sweet cherry fruits, and the disease incidence of the fruits treated with natamycin is the lowest. However, the *Bacillus velezensis* Q-84 serving as an antagonist also has a good inhibitory effect on the postharvest rot of sweet cherry fruits, and is significantly different from the control without any treatment. By *Bacillus velezensis* treatment, the rot process of fruits can be slowed down, and the rot of fruits can be delayed by 2-3 d. Rot of fruit is caused by mass propagation of pathogenic fungi on the fruit surface. It can be seen that the *Bacillus velezensis* Q-84 serving as an antagonist has broad-spectrum antibacterial activity and has an inhibitory effect on a variety of pathogenic fungi.

Example 6 Effects of the Endogenous Antagonist on the Resistance-Related Enzyme Activity of Cherry Fruits A portion near the equator of a sweet cherry was stabbed by a tip of a sterile inoculating needle to form a small hole of 3 mm×3 mm, the wound was inoculated with 20 μL of fermentation broth ($10^9$ CFU/mL) of *Bacillus velezensis* Q-84 serving as an antagonist, sterile water was used as a control, 4 h later, the wound was inoculated with 10 μL of spore suspension ($10^5$ CFU/mL) of *Rhizopus stolonifera* serving as a pathogen, the sweet cherry fruit was stored at room temperature, a sample was taken every 12 h, the enzymatic activity was determined, 20 fruits (the junction of a lesion and a healthy tissue) were sampled each time, and the whole experiment was repeated twice.

Peroxidase (POD) was determined by using guaiacol with reference to Yang X, Jiang X. Antifungal activity and mechanism of tea polyphenols against *Rhizopus stolonifer* [J]. Biotechnology letters, 2015, 37(7): 1463-1472.

Polyphenol oxidase (PPO) was determined by using catechol with reference to Wu S, Zhen C, Wang K, et al. Effects of *Bacillus Subtilis* CF-3 VOCs Combined with Heat Treatment on the Control of *Monilinia fructicola* in Peaches and *Colletotrichum gloeosporioides* in Litchi Fruit[J]. Journal of food science, 2019, 84(12): 3418-3428.

Lipoxygenase (LOX) was determined with reference to Cao Jiankang, Jiang Weibo, and Zhao Yumei. Experiment Guidance of Postharvest Physiology and Biochemistry of Fruits and Vegetables[M]. Beijing: China Light Industry Press, 2007.

Phenylalanine ammonia lyase (PAL) was determined with reference to Arrebola E, Sivakumar D, Bacigalupo R, et al. Combined application of antagonist *Bacillus amyloliquefaciens* and essential oils for the control of peach postharvest diseases[J]. Crop protection, 2010, 29(4): 369-377.

β-1,3-glucanase (GLU) was determined with reference to Lin F, Xue Y, Huang Z, et al. Bacillomycin D inhibits growth of *Rhizopus stolonifer* and induces defense-related mechanism in cherry tomato[J]. Applied microbiology and biotechnology, 2019, 103(18): 7663-7674.

Chitinase (CHI) was determined with reference to Gu R, Zhu S, Zhou J, et al. Inhibition on brown rot disease and induction of defence response in harvested peach fruit by nitric oxide solution[J]. European journal of plant pathology, 2014, 139(2): 369-378.

Figure 14:
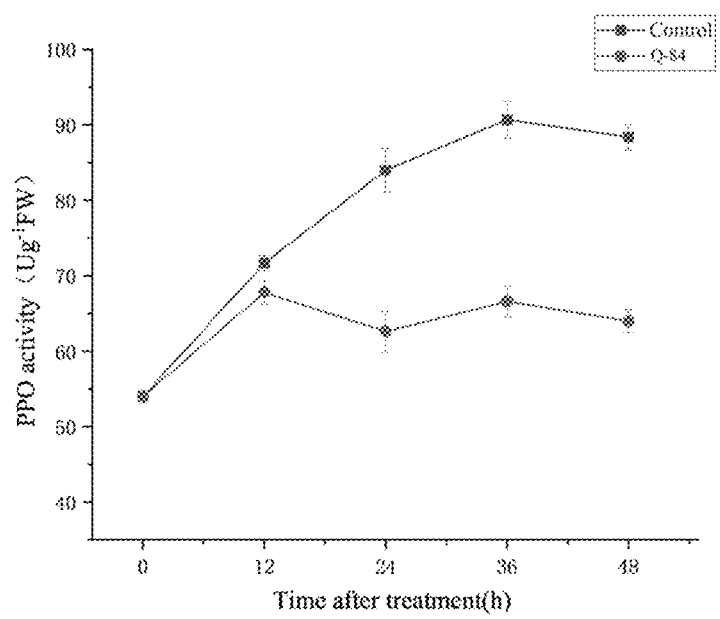
FIG. 14 is a diagram of an effect of the *Bacillus velezensis* Q-84 treatment on the polyphenol oxidase (PPO) activity of the sweet cherry fruit.

6.1 Effect of the Endogenous Antagonist on the Polyphenol Oxidase (PPO) Activity of the Cherry Fruit PPO is the main enzyme that causes browning of fruits and vegetables, and high vigor of PPO will adversely affect the quality of fruits. The PPO activity of the sweet cherry inoculated with the *Bacillus velezensis* Q-84 is shown in FIG. 14. It can be seen from the figure that the PPO activity of the treatment group is lower than that of the control group. The PPO activity shows a roughly increasing trend throughout the treatment period, and the PPO activity of the treatment group fluctuates after reaching the peak at the 12th hour, which is significantly lower than that of the control group. The PPO activity of the control group slightly decreases after reaching the peak at the $36^{th}$ hour. During storage period, the *Bacillus velezensis* Q-84 treatment group shows a low activity, which indicates that the *Bacillus velezensis* Q-84 can inhibit the PPO activity of a cherry fruit, and reduce browning of the fruit.

Figure 15:
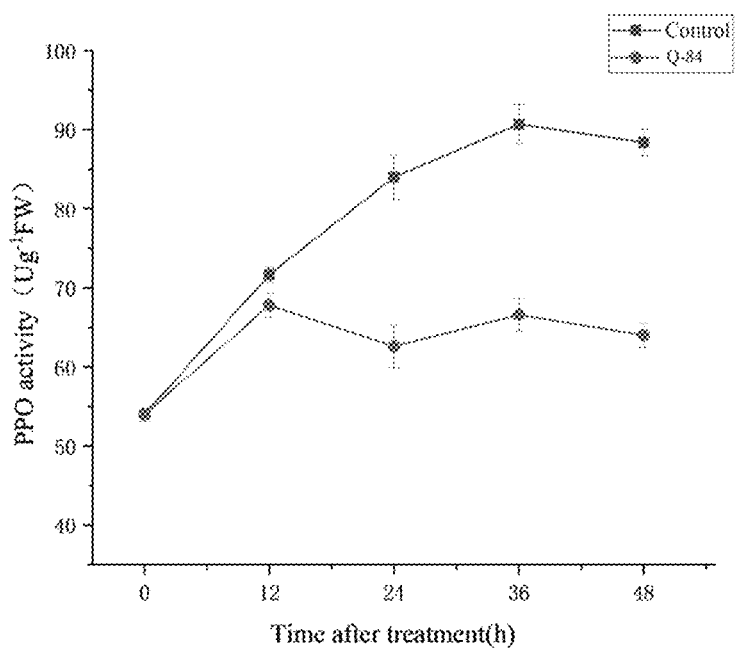
FIG. 15 is a diagram of an effect of the *Bacillus velezensis* Q-84 treatment on the peroxidase (POD) activity of the sweet cherry fruit.

6.2 Effect of the Endogenous Antagonist on the Peroxidase (PPO) Activity of the Cherry Fruit POD is one of the key enzymes of the plant enzymatic defence system, which can catalyse the decomposition of $H_2O_2$ into water, eliminate oxygen free radicals, and relieve the toxicity of $H_2O_2$ to fruits, thereby delaying postharvest decay and improving stress resistance of fruits. The POD activity of the cherry fruit inoculated with the *Bacillus velezensis* Q-84 is shown in FIG. 15. It can be seen from the figure that the POD activities of the treatment group and control group show a trend of first increasing and then decreasing, and reach the peaks at the $36^{th}$ hour, and at this time, the POD activity of the control group is 395 U, and the POD activity of the treatment groups is 470 U, which is 1.18 times that of the control group. After 36 h, the POD activities decrease, but the treatment group also show a high enzyme activity, which is 1.41 times that of the control group. The results indicate that inoculation of the *Bacillus velezensis* Q-84 can obviously induce the increase of the POD activity of a cherry fruit, and improve disease resistance and antioxidant resistance of the cherry fruit.

Figure 16:
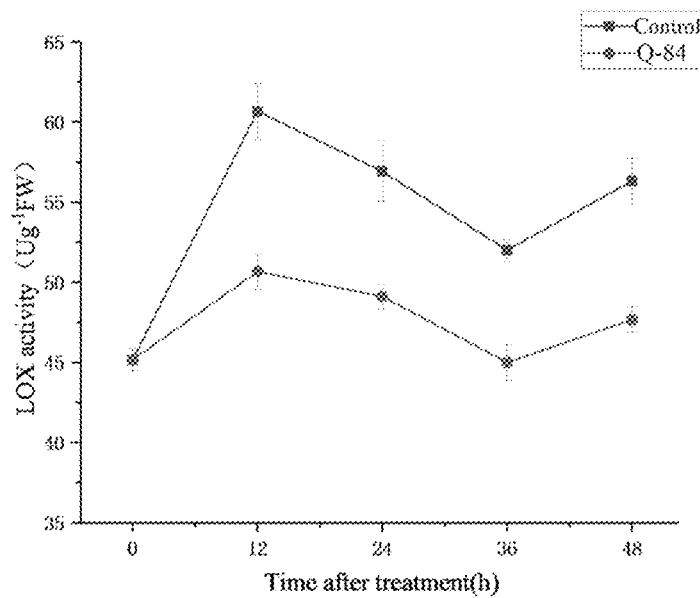
FIG. 16 is a diagram of an effect of the *Bacillus velezensis* Q-84 treatment on the lipoxygenase (LOX) activity of the sweet cherry fruit.

6.3 Effect of the Endogenous Antagonist on the Lipoxygenase (PPO) Activity of the Cherry Fruit LOX is an enzyme that catalyses oxidation of fatty acid of cell membrane, and products of its metabolic way mainly involve in membrane lipid peroxidation, play an important role in the maturation process of fruits, increase the cell membrane permeability, accelerate cell membrane degradation, and generate toxic substances such as free radicals and lipid hydroperoxides at the same time. The LOX activity of the cherry fruit inoculated with the *Bacillus velezensis* Q-84 is shown in FIG. 16. It can be seen from the figure that the LOX activities of the treatment group and the control group show a trend of first increasing and then decreasing. The LOX activity of the control group increases rapidly from $0^{th}$ h to $12^{th}$ h, and reaches the peak of 60.67 U, and at this time, the LOX activity of the treatment group also reaches the peak of 50.16 U. Then, the enzyme activity of the control group decreases but is still kept at a high level, and at the $48^{th}$ h, the enzyme activity of the control group is still 1.38 times that of the treatment group. It indicates that *Bacillus velezensis* Q-84 treatment can inhibit the LOX activity of a cherry fruit caused by *Rhizopus stolonifer*, and reduce the degree of damage to cell membranes caused by free radicals.

Figure 17:
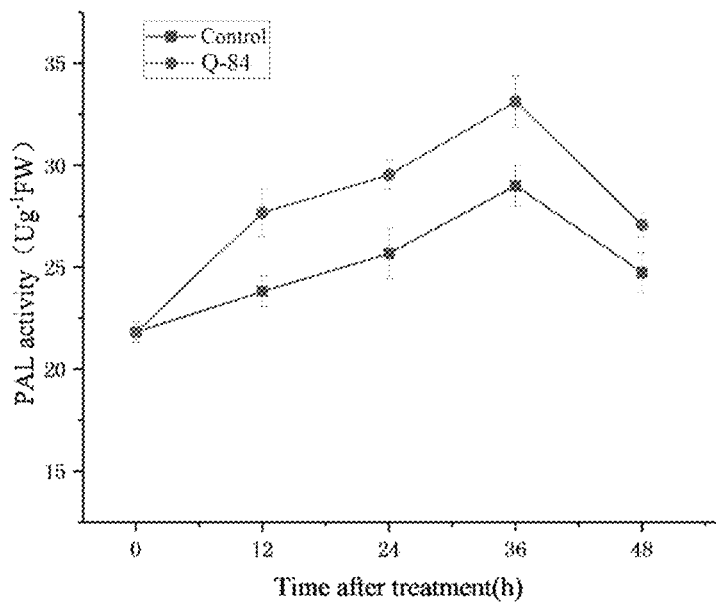
FIG. 17 is a diagram of an effect of the *Bacillus velezensis* Q-84 treatment on the phenylalanine ammonia lyase (PAL) activity of the sweet cherry fruit.

6.4 Effect of the Endogenous Antagonist on the Phenylalanine Ammonia Lyase (PAL) Activity of the Cherry Fruit PAL is the key enzyme of the phenylpropanoid pathway. If disease resistance of a plant is stronger, the PAL activity is higher. The PAL activity of the cherry fruit inoculated with the *Bacillus velezensis* Q-84 is shown in FIG. 17. It can be seen from the figure that the PAL activities of the treatment group and the control group show a trend of first increasing and then decreasing, and reach the peaks at the 36th h, the PAL activity of the treatment group is 33.12 U, which is 1.18 times that of the control group. At the $48^{th}$ h, the PAL activities of the treatment group and the control group decrease to different extents, and the PAL activity of the treatment group is always higher than that of the control group throughout the treatment period. The results indicates that *Bacillus velezensis* Q-84 treatment can further increase the PAL activity of a cherry fruit, and improve the pathogen resistance of the fruit.

Figure 18:
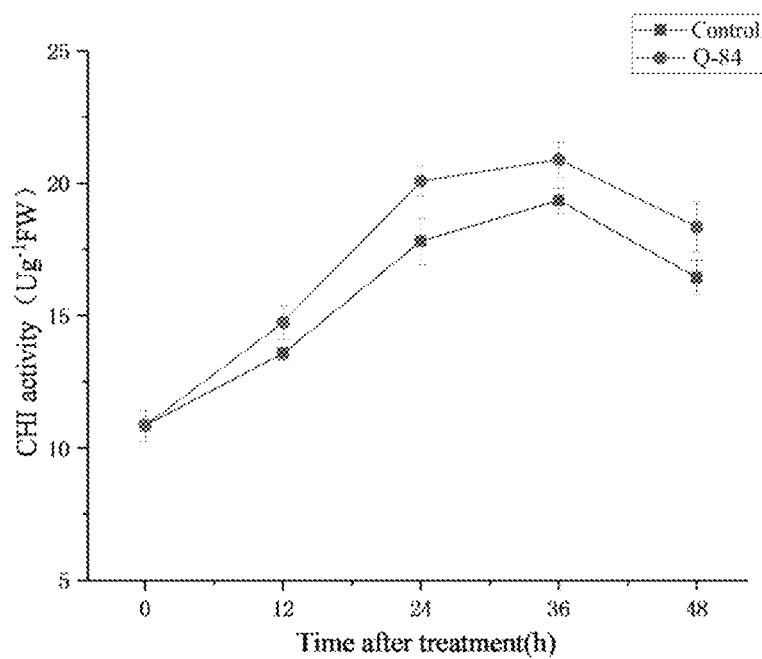
FIG. 18 is a diagram of an effect of the *Bacillus velezensis* Q-84 treatment on the chitinase (CHI) activity of the sweet cherry fruit.

6.5 Effect of the Endogenous Antagonist on the Chitinase (CHI) Activity of the Cherry Fruit The CHI activity of the cherry fruit inoculated with the *Bacillus velezensis* Q-84 is shown in FIG. 18. It can be seen from the figure that the CHI activities of the treatment group and the control group show a trend of first increasing and then decreasing. The enzyme activities of the treatment group and the control group increase rapidly from $0^{th}$ h to $24^{th}$ h, change gently but still increase from $24^{th}$ h to $36^{th}$ h, and reach the peaks at the $36^{th}$ h, and at this time, the CHI activity of the treatment group is 20.08 U, and the CHI activity of the control group is 17.18 U. At the $48^{th}$ h, the CHI activities decrease but are still kept at a high level, and the CHI activity of the treatment group is always higher than that of the control group throughout the treatment period. The results indicate that *Bacillus velezensis* Q-84 treatment can induce the CHI activity of a cherry fruit, and improve disease resistance of the fruit.

Figure 19:
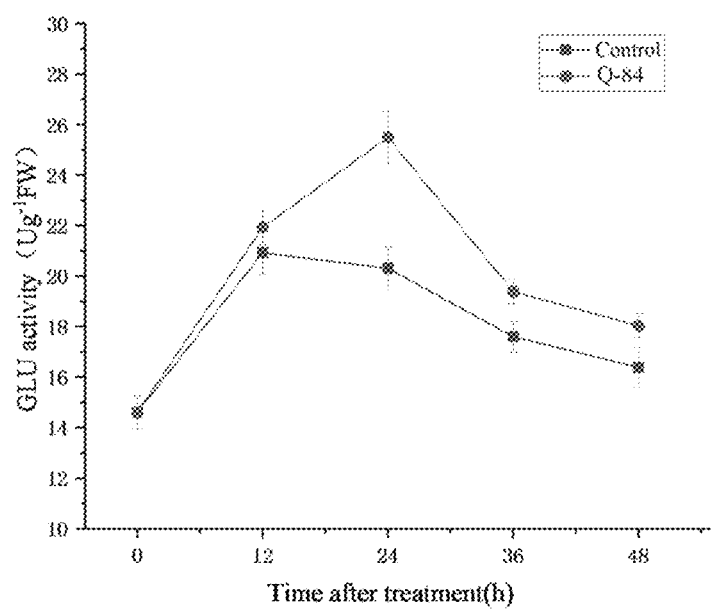
FIG. 19 is a diagram of an effect of the *Bacillus velezensis* Q-84 treatment on the β-1,3-glucanase (GLU) activity of the sweet cherry fruit.

6.6 Effect of the Endogenous Antagonist on the β-1,3-Glucanase (GLU) Activity of the Cherry Fruit GLU is one of the important antifungal substances of a plant. The GLU activity of the cherry fruit inoculated with the *Bacillus velezensis* Q-84 is shown in FIG. 19. It can be seen from the figure that the GLU activities of the treatment group and the control group show a trend of first increasing and then decreasing. The enzyme activities increase rapidly from $0^{th}$ to $12^{th}$ h, the GLU activity of the control group reach the peak of 20.92 U at the 12th h, the GLU activity of the treatment group continuously increases and reaches the peak of 25.49 U at the $24^{th}$ h, which is 1.26 times that of the control group. After 24 h, the GLU activities of the treatment group and the control group decrease, and the enzyme activity of the treatment group is always higher than that of the control group. The results indicate that the *Bacillus velezensis* Q-84 can significantly increase the GLU activity of a sweet cherry fruit.

Based on the above, when applied to the surface of a plant, the *Bacillus velezensis* Q-84 of the present disclosure not only inhibits the pathogen, but also induces disease resistance and oxidation resistance of the plant. It can increase anti-disease enzyme (PAL, CHI, and GLU) activity to improve the disease resistance of the plant, increase the antioxidant enzyme (POD) activity and reduce the PPO and LOX activity at the same time to improve the oxidation resistance of the plant, thereby delaying the postharvest decay and improving stress resistance of fruits.

Comparative Example 1 Effects of the Endogenous Antagonist on the Resistance-Related Enzyme Activity of a Peach Fruit Effects of the *Bacillus velezensis* Q-84 on the resistance-related enzyme of a peach fruit were determined by the method according to Example 6, and a difference was that sterile water and natamycin treatment was taken as a control group, and a treatment group inoculated with the *Bacillus velezensis* Q-84 only was newly added. The POD activity, the LOX activity, the PAL activity, and the CHI activity of the peach fruit inoculated with the *Bacillus velezensis* Q-84 are shown in FIG. 20 to FIG. 23, respectively.

Figure 20:
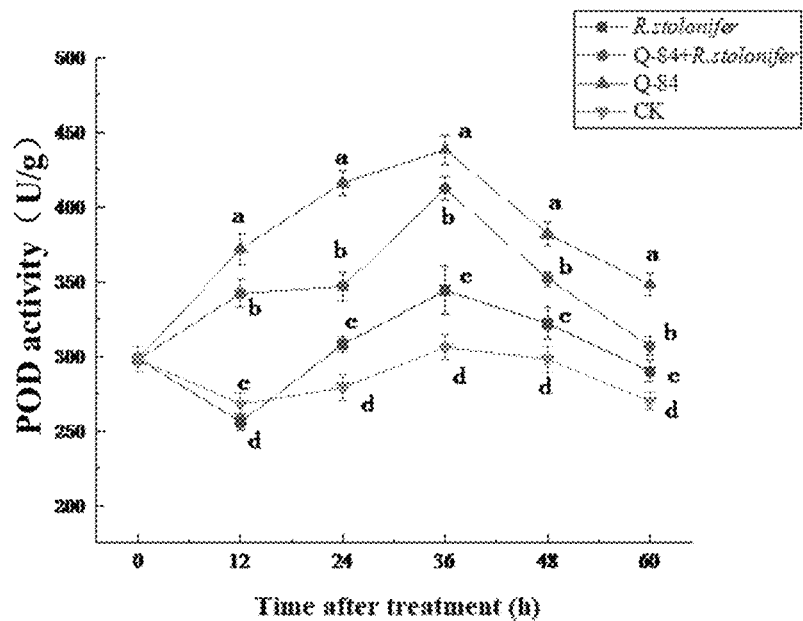
FIG. 20 is a diagram of an effect of *Bacillus velezensis* Q-84 treatment on the peroxidase (POD) activity of a peach fruit, and in the figure, different lowercase letters corresponding to the same time after treatment represent significant differences (p<0.05) among different treatment groups.
Figure 21:
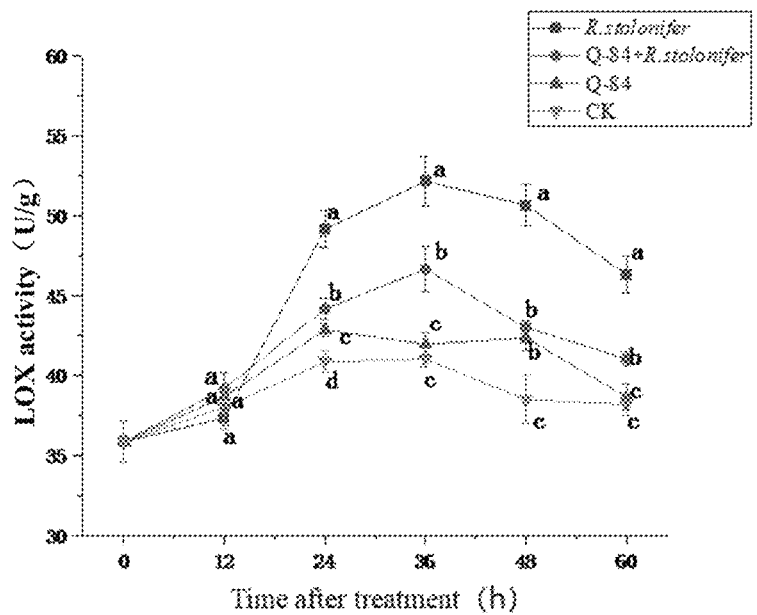
FIG. 21 is a diagram of an effect of the *Bacillus velezensis* Q-84 treatment on the lipoxygenase (LOX) activity of the peach fruit, and in the figure, different lowercase letters corresponding to the same time after treatment represent significant differences (p<0.05) among different treatment groups.
Figure 22:
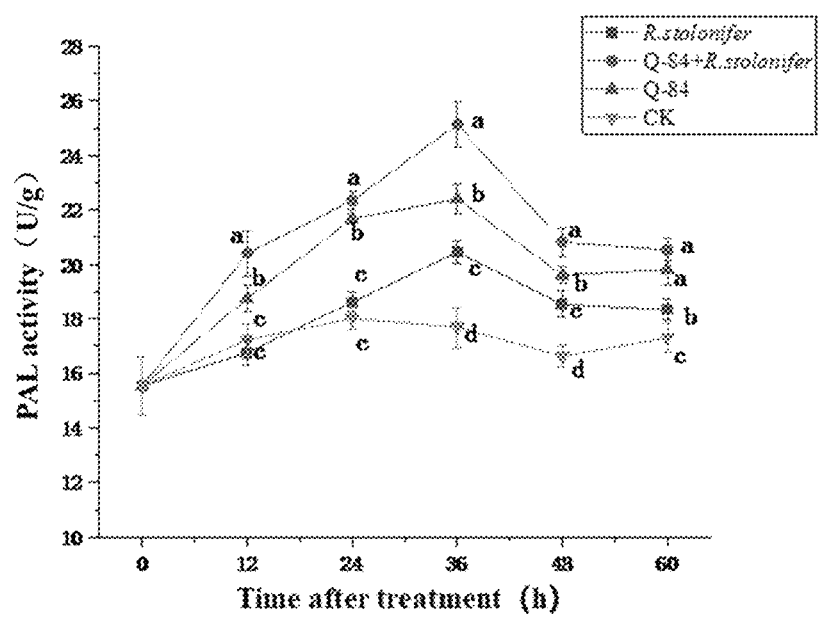
FIG. 22 is a diagram of an effect of the *Bacillus velezensis* Q-84 treatment on the phenylalanine ammonia lyase (PAL) activity of the peach fruit, and in the figure, different lowercase letters corresponding to the same time after treatment represent significant differences (p<0.05) among different treatment groups.
Figure 23:
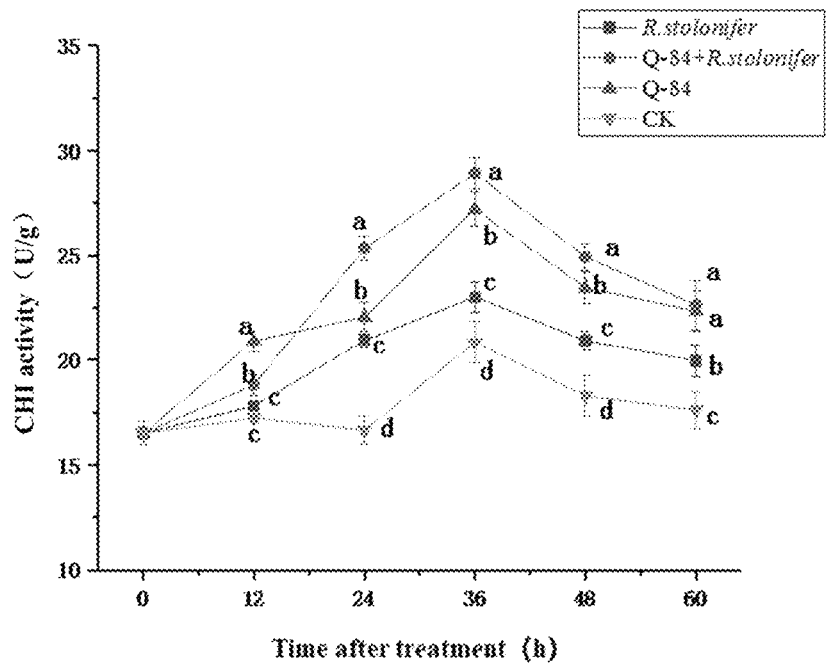
FIG. 23 is a diagram of an effect of the *Bacillus velezensis* Q-84 treatment on the chitinase (CHI) activity of the peach fruit, and in the figure, different lowercase letters corresponding to the same time after treatment represent significant differences (p<0.05) among different treatment groups.

It can be known from FIG. 20 that the POD activities of the treatment groups reach the peaks at the $36^{th}$ h, the POD activity of the treatment group inoculated with the antagonist and the pathogen is 412 U, and the POD activity of the treatment group inoculated with the pathogen only is 344 U. It can be known from FIG. 21 that the peaks of the LOX activities of the treatment group inoculated with the antagonist and the pathogen and the treatment group inoculated with the pathogen only are 46.7 U and 52.12 U, respectively. It can be known from FIG. 22 that the PAL activities of the treatment groups reach the peaks at the $36^{th}$ h, the POD activity of the treatment group inoculated with the antagonist and the pathogen is 25.14 U, and the POD activity of the treatment group inoculated with the pathogen only is 20.46 U. It can be known from FIG. 23 that the CHI activities of the treatment groups reach the peaks at the $36^{th}$ h, the POD activity of the treatment group inoculated with the antagonist and the pathogen is 24.93 U, and the POD activity of the treatment group inoculated with the pathogen only is 23.03 U. Based on the above experimental results, the *Bacillus velezensis* Q-84 can induce disease resistance and oxidation resistance of a peach to a certain extent. However, compared with Example 6, the *Bacillus velezensis* Q-84 can better improve disease resistance and oxidation resistance of a cherry, so it has a certain specificity.

What is claimed is:

1. A method for preventing and treating a microorganism disease of sweet cherry comprising a step of contacting the sweet cherry with *Bacillus velezensis* TA-3-BV deposited in in the China General Microbiological Culture Collection Center (CGMCC) under CGMCC Accession Number: 20398; wherein the microorganism disease is a fungal infection.

2. The method according to claim 1, wherein the fungal is *Rhizopus stolonifera*.

3. A method for improving disease resistance of a plant comprising a step of mixing the plant with *Bacillus velezensis* TA-3-BV deposited in in the China General Microbiological Culture Collection Center (CGMCC) under CGMCC Accession Number: 203981 wherein the plant is a sweet cherry.

4. A method for improving postharvest preservation of sweet cherry comprising a step of contacting the sweet cherry with *Bacillus velezensis* TA-3-BV deposited in in the China General Microbiological Culture Collection Center (CGMCC) under CGMCC Accession Number: 20398.

* * * * *

SEQUENCE LISTING

```
<160> NUMBER OF SEQ ID NOS: 5

<210> SEQ ID NO 1
<211> LENGTH: 1415
<212> TYPE: DNA
<213> ORGANISM: Bacillus velezensis

<400> SEQUENCE: 1
tcgagcggac agatgggagc ttgctccctg atgttagcgg cggacgggtg agtaacacgt      60
gggtaacctg cctgtaagac tgggataact ccgggaaacc ggggctaata ccggatggtt     120
gtttgaaccg catggttcag acataaaagg tggcttcggc taccacttac agatggaccc     180
gcggcgcatt agctagttgg tgaggtaacg gctcaccaag gcaacgatgc gtagccgacc     240
tgagagggtg atcggccaca ctgggactga gacacggccc agactcctac gggaggcagc     300
agtagggaat cttccgcaat ggacgaaagt ctgacggagc aacgccgcgt gagtgatgaa     360
ggttttcgga tcgtaaagct ctgttgttag ggaagaacaa gtgccgttca aatagggcgg     420
caccttgacg gtacctaacc agaaagccac ggctaactac gtgccagcag ccgcggtaat     480
acgtaggtgg caagcgttgt ccggaattat tgggcgtaaa gggctcgcag gcggtttctt     540
aagtctgatg tgaaagcccc cggctcaacc ggggagggtc attggaaact ggggaacttg     600
agtgcagaag aggagagtgg aattccacgt gtagcggtga aatgcgtaga gatgtggagg     660
aacaccagtg gcgaaggcga ctctctggtc tgtaactgac gctgaggagc gaaagcgtgg     720
ggagcgaaca ggattagata ccctggtagt ccacgccgta aacgatgagt gctaagtgtt     780
```

```
aggggggtttc cgcccctaag tgctgcagct aacgcattaa gcactccgcc tggggagtac    840
ggtcgcaaga ctgaaaactca aggaattga cgggggcccg cacaagcggt ggagcatgtg    900
gtttaattcg aagcaacgcg aagaacctta ccaggtcttg acatcctctg acaatcctag    960
agataggacg tccccttcgg gggcagagtg acaggtggtg catggttgtc gtcagctcgt   1020
gtcgtgagat gttgggttaa gtcccgcaac gagcgcaacc cttgatctta gttgccagca   1080
ttcagttggg cactctaagg tgactgccgg tgacaaaccg gaggaaggtg gggatgacgt   1140
caaatcatca tgccccttat gacctgggct acacacgtgc tacaatggac agaacaaagg   1200
gcagcgaaac cgcgaggtta agccaatccc acaaatctgt tctcagttcg gatcgcagtc   1260
tgcaactcga ctgcgtgaag ctggaatcgc tagtaatcgc ggatcagcat gccgcggtga   1320
atacgttccc gggccttgta cacaccgccc gtcacaccac gagagtttgt aacacccgaa   1380
gtcggtgagg taacctttta ggagccagcc gccga                              1415
```

<210> SEQ ID NO 2
<211> LENGTH: 19
<212> TYPE: DNA
<213> ORGANISM: Artificial Sequence
<220> FEATURE:
<223> OTHER INFORMATION: It is synthesized

<400> SEQUENCE: 2
tccgtaggtg aacctgcgg                                                  19

<210> SEQ ID NO 3
<211> LENGTH: 20
<212> TYPE: DNA
<213> ORGANISM: Artificial Sequence
<220> FEATURE:
<223> OTHER INFORMATION: It is synthesized

<400> SEQUENCE: 3
tcctccgctt attgatatgc                                                 20

<210> SEQ ID NO 4
<211> LENGTH: 20
<212> TYPE: DNA
<213> ORGANISM: Artificial Sequence
<220> FEATURE:
<223> OTHER INFORMATION: It is synthesized

<400> SEQUENCE: 4
agagtttgat cctggctcag                                                 20

<210> SEQ ID NO 5
<211> LENGTH: 19
<212> TYPE: DNA
<213> ORGANISM: Artificial Sequence
<220> FEATURE:
<223> OTHER INFORMATION: It is synthesized

<400> SEQUENCE: 5
ggttaccttg ttacgactt                                                  19